(12) United States Patent
Weinberg et al.

(10) Patent No.: US 10,463,871 B2
(45) Date of Patent: Nov. 5, 2019

(54) APPARATUS AND METHOD FOR MEDICAL IMAGE-GUIDED 3-D PRINTING WITHIN A BODY

(71) Applicant: WEINBERG MEDICAL PHYSICS LLC, Bethesda, MD (US)

(72) Inventors: Irving N. Weinberg, Bethesda, MD (US); Aleksandar Nelson Nacev, Bethesda, MD (US); Lamar Odell Mair, Washington, DC (US)

(73) Assignee: Weinberg Medical Physics Inc MD (US)

( * ) Notice: Subject to any disclaimer, the term of this patent is extended or adjusted under 35 U.S.C. 154(b) by 585 days.

(21) Appl. No.: 15/053,762

(22) Filed: Feb. 25, 2016

(65) Prior Publication Data

US 2016/0243377 A1 Aug. 25, 2016

Related U.S. Application Data

(60) Provisional application No. 62/120,584, filed on Feb. 25, 2015.

(51) Int. Cl.
*A61N 2/02* (2006.01)

(52) U.S. Cl.
CPC ...................... *A61N 2/02* (2013.01)

(58) Field of Classification Search
CPC ........................................ A61N 2/02
See application file for complete search history.

(56) References Cited

U.S. PATENT DOCUMENTS

| | | | |
|---|---|---|---|
| 2007/0048383 A1 | 3/2007 | Helmus | |
| 2011/0003003 A1* | 1/2011 | Goldberg | A61K 41/00 424/490 |
| 2011/0160515 A1 | 6/2011 | Feucht | |
| 2011/0177590 A1 | 7/2011 | Clyne | |
| 2013/0046169 A1* | 2/2013 | Weinberg | A61B 5/055 600/411 |
| 2014/0309479 A1 | 10/2014 | Weinberg | |

OTHER PUBLICATIONS

International Search Report and Written Opinion for corresponding PCT/US2016/019594 dated May 11, 2016.

* cited by examiner

*Primary Examiner* — Thaddeus B Cox
(74) *Attorney, Agent, or Firm* — Barnes & Thornburg LLP

(57) ABSTRACT

Disclosed embodiments enable apparatus and methodologies that are provided for three-dimensional construction of tissues in the body at locations internal to the body.

21 Claims, 2 Drawing Sheets

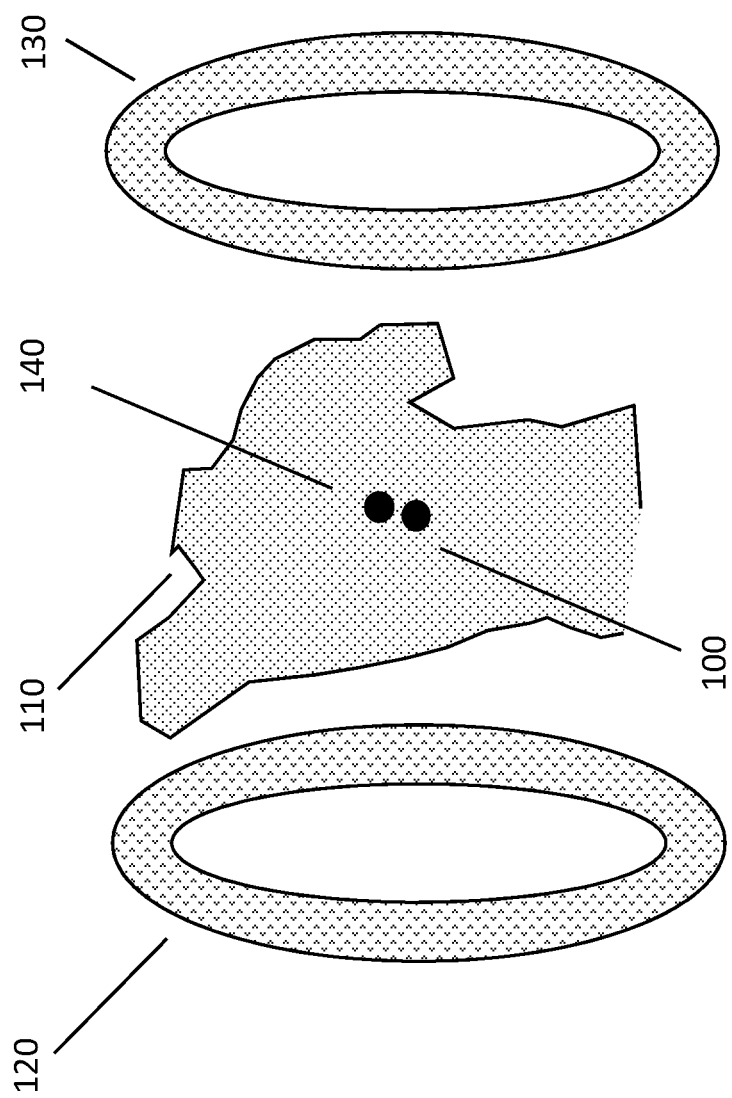

APPARATUS AND METHOD FOR MEDICAL IMAGE-GUIDED 3-D PRINTING WITHIN A BODY

CROSS-REFERENCE TO RELATED APPLICATION(S)

This application relies for priority on U.S. Provisional Patent Application Ser. No. 62/120,584, entitled "MEDICAL APPLICATION OF CONTACTLESS IN SITU IMAGE GUIDED 3-D PRINTING," filed on Feb. 25, 2015, the entirety of which being incorporated by reference herein.

FIELD

Disclosed embodiments are directed, generally, to medical therapy.

BACKGROUND

"3-D bio-printing" is a term defined as the stepwise assembly of an organ or tissues outside the body. "In situ 3-D printing" has been defined as bio-printing onto externally-accessible organs or tissues that are part of a body.

SUMMARY

The following presents a simplified summary in order to provide a basic understanding of some aspects of various invention embodiments. The summary is not an extensive overview of the invention. It is neither intended to identify key or critical elements of the invention nor to delineate the scope of the invention. The following summary merely presents some concepts of the invention in a simplified form as a prelude to the more detailed description below.

In accordance with disclosed embodiments, apparatus and methodologies are provided for three-dimensional construction of tissues in the body at locations internal to the body.

BRIEF DESCRIPTION OF FIGURES

A more complete understanding of the disclosed embodiments and the utility thereof may be acquired by referring to the following description in consideration of the accompanying drawings, in which like reference numbers indicate like features, and wherein:

FIG. 2 illustrates a subsequent step in which an additional cell or biomaterial has been deposited adjacent to the previously placed cell or biomaterial under the imaging guidance and/or propulsion provided by coil structures.

DETAILED DESCRIPTION

Figure 1:
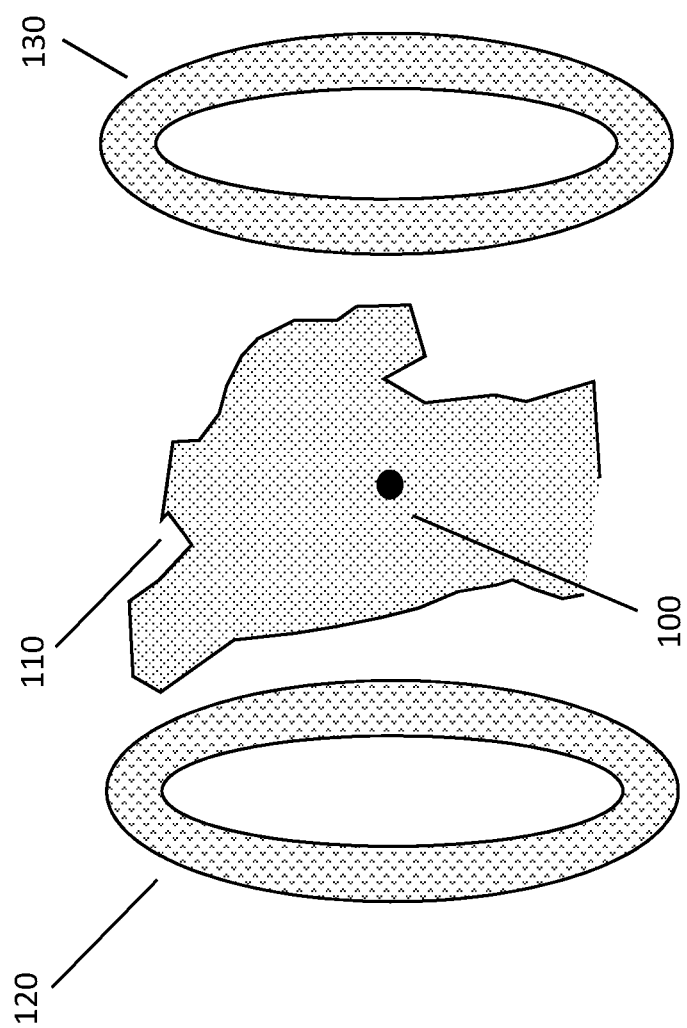
FIG. 1 illustrates an apparatus for the deposition of at least one cell or biomaterial containing magnetic material within a body under the imaging guidance and/or propulsion provided by one or more coil structures, at least one of which is at least in part external to the body.

The description of specific embodiments is not intended to be limiting. To the contrary, those skilled in the art should appreciate that there are numerous variations and equivalents that may be employed without departing from the scope of the present invention. Those equivalents and variations are intended to be encompassed by the present invention.

In the following description of various embodiments, reference is made to the accompanying drawings, which form a part hereof, and in which is shown, by way of illustration, various embodiments in which the invention may be practiced. It is to be understood that other embodiments may be utilized and structural and functional modifications may be made without departing from the scope and spirit of the present invention.

Moreover, it should be understood that various connections are set forth between elements in the following description; however, these connections in general, and, unless otherwise specified, may be either direct or indirect, either permanent or transitory, and either dedicated or shared, and that this specification is not intended to be limiting in this respect.

Disclosed embodiments may utilize and/or be implemented in combination with various prior inventions reported by Weinberg, including application Ser. No. 13/586,489, entitled "MRI-Guided Nanoparticle Cancer Therapy Apparatus and Methodology", application Ser. No. 13/761,200, entitled "Equipment and Methodology for Magnetically-Assisted Delivery of Therapeutic Agents through Barriers", application Ser. No. 14/182,488, entitled "System, Method and Equipment for Implementing Temporary Diamagnetic Propulsive Focusing Effect with Transient Applied Magnetic Field Pulses", U.S. Pat. No. 8,154,286, entitled "Apparatus and Method for Decreasing Bio-Effects of Magnetic Fields", as well as U.S. provisional application Ser. No. 62/292,945, by Aleksandar Nacev, entitled "Method and Apparatus for Manipulating Electropermanent Magnets for Magnetic Resonance Imaging and Image Guided Therapy", and other patents and applications sharing priority claims with those applications (the entirety of which being incorporated by reference herein).

Disclosed embodiments may provide an apparatus and method for constructing structures and/or body parts (for example, organs) inside the body. The body may be human or of another animal. It is to be understood that the term "body part" is meant to include multiple cases, for example, an entire body part (for example, the right kidney), a section of a body part (for example, the lower pole of the right kidney), or a new body part or structure in the body that may be useful (for example, a depot for slow drug release, an electrical stimulator, etc.).

It is further to be understood that construction of a body part may proceed in a stepwise manner upon a substrate (for example, on the diaphragm, on a mesentery, on an artificial membrane, etc.) or upon an existing part (for example, a formed or damaged kidney) or upon biomaterials previously deposited by the disclosed embodiments or by other means.

It is understood that the location within the body of the body part to be constructed or added to is termed the "target location".

FIG. 1 illustrates the deposition of a cell or biomaterial 100 containing magnetic material within a body 110 under the imaging guidance and/or propulsion provided by one or more coil structures 120 and/or 130, at least one of which is at least in part external to the body. FIG. 2 illustrates a subsequent operation in which an additional cell or biomaterial 140 has been deposited adjacent to the previously placed cell or biomaterial 100 under the imaging guidance and/or propulsion provided by coil structures 120 and 130.

It is to be understood that coil structures 120 and/or 130 may be simple coils as represented in the figures, or may be much more complex coils (whether made of copper or superconducting or other materials) and/or arrays (whether in coil form or not) of permanent or electro-permanent magnets, or combinations of such materials.

It is further to be understood that power supplies, computers, wires, and other electronic components may be used to activate and control the magnetic and electric fields created by coil structures 120 and/or 130 or other nearby coils or wires. It is understood that the computer may be part of a controller, which controls operation of coil structures 120 and/or 130, and may control other operations.

It is to be understood that the term "coil structures" includes the possibility that some portion of these structures may be used to receive or transmit electrical energy (for example, in the radiofrequency range) or magnetic energy.

It is to be understood that, although the coil structures 120 and 130 are shown as two distinct structures on two sides of the body, in at least one embodiment, it is possible that the magnetic functions of such coil structures may be implemented with one or more coils arrayed on only one side of the body (for example with 120 alone).

In accordance with at least one embodiment, biomaterials may be infused with magnetizable particles. For the purposes of this description, the term "biomaterials" is to be understood to include non-living (for example, protein scaffolds, biopolymers, biocompatible circuitry) or living materials (for example, cells) or a combination of living and non-living materials (for example, a bio-film). One way to perform such infusion may be to grow cells in a culture whose medium contains magnetizable particles or solution. After the biomaterials have been infused with magnetizable materials, the cells may be introduced into a body. For the purpose of this specification, the term "magnetizable materials" may include both solutions and particles containing magnetizable elements or compounds. This introduction of cells may occur at a location distant from the target location. The introduction may be through a vessel, native orifice, artificial orifice, the skin, or some other method. In an alternative embodiment, magnetic materials (for example, magnetizable particles in a solution) may be introduced into the body so as to guide, glue, or otherwise assist in assembly of the biomaterials within the body. Such an introduction may be implemented as a separate operation, or near the time of the introduction of the biomaterials into the body.

The biomaterials may be transported to the target location in several ways. In at least one embodiment, the biomaterials may circulate through the body more or less randomly, and be concentrated in a target location under the influence of a magnetic field, for example through the establishment of a maximal magnetic field near or at the target location. For the purposes of this specification, the term "magnetic field" includes magnetic gradient or gradients. Alternatively, the biomaterials may be attracted to the location of or near the target via biological attractive means (e.g., antibodies on the surface of the biomaterials that bind to tissues at or near the target location). Alternatively, the biomaterials may be activated (for example, undergo a conformal change) upon change in pH or chemical environment near or in the target location so as to remain in that vicinity. Alternately, the biomaterials may be introduced to a location of or near the target via conventional surgery or catheters. Alternatively, the biomaterials may be transported actively to a target via magnetic fields controlled under imaging guidance, for example as disclosed in an earlier invention by Irving Weinberg (U.S. patent application Ser. No. 13/586,489, entitled "MRI-Guided Nanoparticle Therapy Apparatus and Methodology"), incorporated by reference in its entirety. The particles may be propelled as in PCT/US2015/058617, International application entitled "Method and Apparatus for Non-Contact Axial Particle Rotation and Decoupled ParticlePropulsion". Or, one or more of the above alternative means may be used in combination to bring the biomaterials in the vicinity of a target location.

Once in the vicinity of the target location, the biomaterials may be concentrated or positioned in or near the target location under imaging guidance from coil structures 120 and/or 130, for example using means described in an earlier invention by Irving Weinberg (U.S. patent application Ser. No. 14/182,488, entitled "System, Method and Equipment for Implementing Temporary Diamagnetic Propulsive Focusing Effect with Transient Applied Magnetic Field Pulses"), incorporated by reference in its entirety. Such concentration method may be used to assemble the biomaterials in appropriate locations for tissue repair, augmentation, or genesis as desired, within one or multiple sessions. As in prior art examples of 3-D bioprinting (that are not performed in the body), the concentration of biomaterials upon a substrate or upon previously deposited biomaterials may be performed in a successive manner in order to form a functional structure, for example a kidney.

It is to be understood that the term "functional" may include structural roles (for example, to bolster or replace a collapsed vertebra), delivery roles (for example, to produce a hormone, medication, or other substance in the body), mechanical roles (for example, to pump or transmit blood, lymph, or other substances), sensorimotor roles (for example, to transmit an electrical pulse to or from a neuron or muscle), or a combination of one or more of the above-mentioned roles.

As disclosed in the prior Weinberg inventions, imaging may be accomplished by application of radiofrequency (RF) and/or magnetic gradient pulses that are delivered between or during the magnetic field pulses used to propel the particles. Energy may be delivered by the apparatus to particles in the biomaterials, either from RF transmission coils or from magnetic pulses, in order to assist in assembly or cohesion of the biomaterials. Cohesion of the biomaterials to a substrate or to previously deposited biomaterials may be accomplished at least in part through magnetic attraction of the magnetic components of the biomaterials to one another, at least in part under the influence of the external magnetic field supplied by coil structures 120 and/or 130. Cohesion may be accomplished through heating of the biomaterials, for example by employing alternating magnetic fields emitted by coil structures 120 and/or 130 or other coil structures or wires in or near the body. Alternatively, cohesion may be accomplished through motion of one or more portions of the biomaterials caused by magnetic fields emitted by coil structures 120 and/or 130 or other coil structures or wires in or near the body, in which the motion causes release of adherent substances from the biomaterials (for example, entactin or other extracellular matrix protein).

It is understood that assembly of the biomaterials may be more readily accomplished when coil structures 120 and/or 130 can be activated magnetically in order to accomplish magnetic resonance imaging, and then deactivated so as not to affect the configuration of the assembled biomaterials. This changing magnetic activation status may be accomplished economically using the electropermanent approach described in the provisional patent application 62/292,945 by Aleksandar Nacev entitled "Method and Apparatus for Manipulating Electropermanent Magnets for Magnetic Resonance Imaging and Image Guided Therapy" (the entirety of which being incorporated by reference herein). The ability to change the magnetic field permits the apparatus to alternately function as a magnetic resonance imaging device, a magnetic particle imaging device, and a particle propulsion device. Alternatively, propulsion of magnetic materials may be accomplished in the presence of a static magnetic field, as taught in the patent application Ser. No. 14/873,738 by Nacev entitled "Pulsed Gradient Field Method to Counteract a Static Magnetic Field for Magnetic Particle Focusing" (the entirety of which being incorporated by reference herein). It is to be understood that the biomaterials may include substances that allow visualization through means other than magnetic resonance imaging, for example they may include radioactive or fluorescent substances.

Magnetic materials may be visualized with the apparatus by using magnetic particle imaging, or alternatively through the use of the method taught in provisional patent application USA 62/255,843 entitled "Method and Apparatus for high slew rate single point magnetic resonance imaging of magnetizable nanoparticles" (the entirety of which being incorporated by reference herein).

It is to be understood that the assembly of biomaterials may be more readily accomplished with very high spatial resolution, which may be accomplished by using the very fast pulse sequences and/or gradients enabled by U.S. Pat. No. 8,154,286, entitled "Apparatus and Method for Decreasing Bio-Effects of Magnetic Fields" (the entirety of which being incorporated by reference herein). These fast pulse sequences allow many data collections to occur for a given acquisition period, thereby increasing signal-to-noise ratio for small voxels and allowing high spatial resolution.

It is to be understood that rotatory and/or translational motion may be applied to magnetic biomaterials or to magnetic materials in the vicinity of biomaterials, again for example as in PCT/US2015/058617 application, entitled "Method and Apparatus for Non-Contact Axial Particle Rotation and Decoupled Particle Propulsion" (the entirety of which being incorporated by reference herein).

It is to be understood that the use of imaging with assembly may constitute a closed-loop feedback to assist in user control of the magnetic fields required for assembly of the biomaterials, and thereby assist in facilitating effective assembly.

It is to be understood that the above disclosed embodiments may be used in combination with other medical devices, for example, ultrasound or x-ray computed tomography or nuclear medicine, in order to better accomplish imaging guidance or propulsion or assembly of biomaterials.

In accordance with at least some disclosed embodiments, the system may provide the ability to receive feedback on the printing ability of the system and/or provide optimization. For example, the structure and desired function of the printed "part" may be examined and or changed per a user's request.

In accordance with at least some disclosed embodiments, the system may provide the ability to pump fluids, assemble electronic components/circuits, absorb toxins, attract specific types of cells or otherwise use the disclosed embodiments to affect the in situ environment within subjects, human and otherwise.

While disclosed embodiments have been described in conjunction with the specific embodiments outlined above, it is evident that many alternatives, modifications and variations will be apparent to those skilled in the art. Accordingly, the various embodiments of the invention, as set forth above, are intended to be illustrative, not limiting. Various changes may be made without departing from the spirit and scope of the invention.

Additionally, it should be understood that the functionality described in connection with various described components of various embodiments may be combined or separated from one another in such a way that the architecture of the resulting system is somewhat different than what is expressly disclosed herein. Moreover, it should be understood that, unless otherwise specified, there is no essential requirement that methodology operations be performed in the illustrated order; therefore, one of ordinary skill in the art would recognize that some operations may be performed in one or more alternative order and/or simultaneously.

Various components of the invention may be provided in alternative combinations operated by, under the control of or on the behalf of various different entities or individuals.

Further, it should be understood that, in accordance with at least one embodiment of the invention, system components may be implemented together or separately and there may be one or more of any or all of the disclosed system components. Further, system components may be either dedicated systems or such functionality may be implemented as virtual systems implemented on general purpose equipment via software implementations.

As a result, it will be apparent for those skilled in the art that the illustrative embodiments described are only examples and that various modifications can be made within the scope of the invention as defined in the appended claims.

What is claimed:

1. An apparatus for assembling biomaterials in a body into or onto functional body parts, the apparatus comprising:
    at least one coil structure external to the body that applies an electromagnetic field to the biomaterials in the body under imaging guidance, and
    biomaterials,
    wherein the biomaterials contain, or are near, magnetic materials in the body,
    wherein the biomaterials are in the vicinity of the magnetic materials wherein the biomaterials are assembled, in part, using temporary diamagnetic propulsive focusing effect with transient applied magnetic field pulses.

2. The apparatus of claim 1, further comprising a controller that is coupled to and controls the at least one coil structure to control the electromagnetic field created by the at least one coil structure to change in time.

3. The apparatus of claim 1, wherein the electromagnetic field created is controlled by control unit to vary in space by controlling the magnetic field gradient.

4. The apparatus of claim 1, wherein the biomaterials are assembled successively within the body under imaging guidance into a functional structure.

5. The apparatus of claim 1, wherein the biomaterials are assembled, in part, using heating of magnetic materials with alternating magnetic fields.

6. The apparatus of claim 1, wherein the biomaterials are assembled, in part, using magnetic attraction between magnetic materials in the body.

7. The apparatus of claim 1, wherein the biomaterials are assembled, in part, using materials released by the biomaterials under the influence of an electromagnetic field emitted by at least one coil structure external to the body.

8. The apparatus of claim 1, wherein the apparatus assembles the biomaterials into an assembled functional body part and the assembled functional body part delivers a substance in the body.

9. The apparatus of claim 1, wherein the apparatus assembles the biomaterials into an assembled functional body part and the assembled functional body part provides structural support in the body.

10. The apparatus of claim 1, wherein the apparatus assembles the biomaterials into an assembled functional body part and the assembled functional body part provides mechanical support in the body.

11. The apparatus of claim 1, wherein the apparatus assembles the biomaterials into an assembled functional body part and the assembled functional body part provides sensorimotor function in the body.

12. A method for assembling biomaterials in a body into or onto functional body parts, the method comprising:
applying, via at least one coil structure external to the body, an electromagnetic field to the biomaterials in the body under imaging guidance,
wherein said biomaterials contain, or are near, magnetic materials in the body,
wherein the biomaterials are in the vicinity of the magnetic materials, and assembling the biomaterials, in part, using temporary diamagnetic propulsive focusing effect with transient applied magnetic field pulses.

13. The method of claim 12, further comprising controlling the electromagnetic field created by the at least one coil structure to change over time.

14. The method of in claim 12, further comprising assembling the biomaterials successively within the body under imaging guidance into a functional structure.

15. The method of claim 12, further comprising assembling the biomaterials, in part, using heating of magnetic materials with alternating magnetic fields.

16. The method of claim 12, further comprising assembling the biomaterials, in part, using magnetic attraction between magnetic materials in the body.

17. The method of claim 12, wherein the biomaterials are assembled, in part, using materials released by the biomaterials under the influence of an electromagnetic field emitted by at least one coil structure external to the body.

18. The method of claim 12, further comprising assembling the biomaterials into an assembled functional body part, wherein the assembled functional body part delivers a substance in the body.

19. The method of claim 12, further comprising assembling the biomaterials into an assembled functional body part, wherein the assembled functional body part provides structural support in the body.

20. The method of claim 12, further comprising assembling the biomaterials into an assembled functional body part, wherein the assembled functional body part provides mechanical support in the body.

21. The method of claim 12, further comprising assembling the biomaterials into an assembled functional body part, wherein the assembled functional body part provides sensorimotor function in the body.

* * * * *